(12) United States Patent
Ridley et al.

(10) Patent No.: US 8,152,724 B2
(45) Date of Patent: *Apr. 10, 2012

(54) ULTRASOUND GUIDED PROBE DEVICE AND METHOD OF USING SAME

(75) Inventors: Stephen F. Ridley, Columbia, SC (US); M. Dexter Hagy, Greenville, SC (US)

(73) Assignee: Soma Access Systems, LLC, Greenville, SC (US)

( * ) Notice: Subject to any disclaimer, the term of this patent is extended or adjusted under 35 U.S.C. 154(b) by 651 days.

This patent is subject to a terminal disclaimer.

(21) Appl. No.: 11/787,290

(22) Filed: Apr. 16, 2007

(65) Prior Publication Data

US 2007/0208255 A1    Sep. 6, 2007

Related U.S. Application Data

(63) Continuation of application No. 10/705,784, filed on Nov. 11, 2003, now Pat. No. 7,244,234.

(51) Int. Cl.
*A61B 8/00* (2006.01)

(52) U.S. Cl. .................................................. 600/443

(58) Field of Classification Search .......... 600/461–464, 600/437, 459, 465–467, 443, 439, 471; 606/1; 128/918

See application file for complete search history.

(56) References Cited

U.S. PATENT DOCUMENTS

| | | |
|---|---|---|
| 3,721,227 A | 3/1973 | Larson et al. |
| 4,029,084 A | 6/1977 | Soldner |
| 4,044,273 A | 8/1977 | Kanda et al. |
| 4,108,165 A | 8/1978 | Kopp et al. |
| 4,249,539 A | 2/1981 | Vilkomerson et al. |
| 4,289,139 A | 9/1981 | Enjoji et al. |
| 4,491,137 A | 1/1985 | Jingu |
| 4,671,292 A | 6/1987 | Matzuk |
| 4,681,103 A | 7/1987 | Boner et al. |
| 4,742,829 A | 5/1988 | Law et al. |
| 4,838,506 A | 6/1989 | Cooper |
| 5,078,144 A | 1/1992 | Sekino et al. |
| 5,119,818 A | 6/1992 | Carroll et al. |
| 5,261,409 A | 11/1993 | Dardel |
| 5,291,090 A | 3/1994 | Dias |
| 5,329,927 A | 7/1994 | Gardineer et al. |
| 5,341,810 A | 8/1994 | Dardel |

(Continued)

FOREIGN PATENT DOCUMENTS

EP    0617922 A1    3/1994

(Continued)

OTHER PUBLICATIONS

Article—The SMART needle, *Anesthesia*, vol. 49, 1994, pp. 889-891.

(Continued)

*Primary Examiner* — Tse Chen
*Assistant Examiner* — Elmer Chao
(74) *Attorney, Agent, or Firm* — Dority & Manning, P.A.

(57) ABSTRACT

The present invention is directed to devices and methods for use in ultrasound guiding of percutaneous probes during medical procedures. The ultrasound devices of the present invention include an ultrasound transducer. The devices can also include means and methods for imaging a virtual probe overlaying the sonogram formed by the ultrasound device such that a real time image of the probe approach to the target may be observed during and after probe placement.

15 Claims, 9 Drawing Sheets

U.S. PATENT DOCUMENTS

| | | | |
|---|---|---|---|
| 5,490,522 | A | 2/1996 | Dardel |
| 5,494,039 | A | 2/1996 | Onik et al. |
| 5,758,650 | A | 6/1998 | Miller et al. |
| 5,871,448 | A | 2/1999 | Ellard |
| 5,924,992 | A | 7/1999 | Park et al. |
| 5,928,219 | A | 7/1999 | Friend et al. |
| 5,941,889 | A | 8/1999 | Cermak |
| 5,971,949 | A | 10/1999 | Levin et al. |
| 6,017,316 | A | 1/2000 | Ritchart et al. |
| 6,027,457 | A | 2/2000 | Shmulewitz et al. |
| 6,138,495 | A | 10/2000 | Paltieli et al. |
| 6,206,832 | B1 | 3/2001 | Downey et al. |
| 6,216,029 | B1 | 4/2001 | Paltieli |
| 6,261,234 | B1 | 7/2001 | Lin |
| 6,296,614 | B1 * | 10/2001 | Pruter .......................... 600/461 |
| 6,336,899 | B1 | 1/2002 | Yamazaki |
| 6,361,499 | B1 | 3/2002 | Bates et al. |
| 6,379,307 | B1 | 4/2002 | Filly et al. |
| 6,398,711 | B1 | 6/2002 | Green et al. |
| 6,409,686 | B1 | 6/2002 | Guthrie et al. |
| 6,443,902 | B1 | 9/2002 | Sasady |
| 6,457,365 | B1 | 10/2002 | Stephens et al. |
| 6,475,152 | B1 | 11/2002 | Kelly et al. |
| 6,527,731 | B2 | 3/2003 | Weiss et al. |
| 6,554,771 | B1 | 4/2003 | Buil et al. |
| 6,582,368 | B2 | 6/2003 | Holdaway et al. |
| 6,626,832 | B1 | 9/2003 | Paltieli et al. |
| 6,690,159 | B2 | 2/2004 | Burreson et al. |
| 6,755,789 | B2 | 6/2004 | Stringer et al. |
| 6,758,817 | B1 | 7/2004 | Pruter et al. |
| 6,764,449 | B2 | 7/2004 | Lee et al. |
| 2001/0031941 | A1 | 10/2001 | Edwards et al. |
| 2002/0082518 | A1 | 6/2002 | Weiss et al. |
| 2002/0123689 | A1 | 9/2002 | Furia |
| 2002/0156376 | A1 | 10/2002 | Wang et al. |
| 2002/0173719 | A1 | 11/2002 | Zhao et al. |
| 2002/0183740 | A1 | 12/2002 | Edwards et al. |
| 2003/0036709 | A1 | 2/2003 | Jordan, III |
| 2003/0097066 | A1 | 5/2003 | Shelby et al. |
| 2003/0100814 | A1 | 5/2003 | Kindlein |
| 2003/0120154 | A1 | 6/2003 | Sauer et al. |
| 2003/0120155 | A1 | 6/2003 | Sauer et al. |
| 2003/0163142 | A1 | 8/2003 | Paltieli et al. |
| 2003/0171681 | A1 | 9/2003 | Weilandt |
| 2003/0233046 | A1 | 12/2003 | Ferguson et al. |
| 2004/0034297 | A1 | 2/2004 | Darrow et al. |
| 2004/0097805 | A1 | 5/2004 | Verard et al. |
| 2004/0131299 | A1 | 7/2004 | Adoram et al. |
| 2004/0133111 | A1 | 7/2004 | Szczech et al. |
| 2004/0133168 | A1 | 7/2004 | Salcudean et al. |
| 2004/0143252 | A1 | 7/2004 | Hurst |

FOREIGN PATENT DOCUMENTS

| | | |
|---|---|---|
| JP | 56-43941 | 4/1981 |
| JP | 57-122861 | 7/1982 |
| JP | 59-007919 | 1/1984 |
| JP | 63-195803 | 12/1988 |
| JP | 1-110707 | 7/1989 |
| JP | 06-205776 | 7/1994 |
| JP | 7-506997 | 8/1995 |
| JP | 08-000614 | 1/1996 |
| JP | 08-229042 | 9/1996 |
| JP | 10005223 | 1/1998 |
| JP | 10-57376 | 3/1998 |
| JP | 2002-112998 | 4/2002 |
| JP | 09-322880 | 12/2007 |
| WO | 00/57767 | 10/2000 |

OTHER PUBLICATIONS

Product Information from Hitachi, Probes and Systems, 5 pages.
Making Health Care Safer: A Critical Analysis of Patient Safety Practices, Evidence Report/Technology Assessment, No. 43, Jul. 20, 2001, Preface and Table of Contents—i-x, Summary—1-8, Chapter 21, Ultrasound Guidance of Central Vein Catheterization—245-253.
Product Information Sheet for Biopsy Probe EUP-B31 from Hitachi www.hitachimed.com, Sep. 22, 2003.
Product Information Sheet on Probe Covers & Surgical Drapes from Protek Medical Products, Inc., 2 pages.
Supplementary European Search Report for Application No. PCT/US2004037268, Oct. 31, 2007.
JP App. No. 2006539726 Office Action dated Jun. 1, 2010.
JP App. No. 2006539726 Office Action dated Sep. 28, 2010.

* cited by examiner

ULTRASOUND GUIDED PROBE DEVICE AND METHOD OF USING SAME

CROSS REFERENCE TO RELATED APPLICATIONS

The present application is a continuation application of U.S. patent application Ser. No. 10/705,784, now U.S. Pat. No. 7,244,234 having a filing date of Nov. 11, 2003.

BACKGROUND OF THE INVENTION

Medical probe devices are utilized for many purposes, chief of which include catheterization, centesis, and biopsy procedures. Percutaneous placement of probes using these devices is often performed with techniques which rely on palpable or visible structures. This is neither a simple nor a risk-free procedure. For instance, proper insertion and placement of a percutaneous probe depends on correct localization of anatomical landmarks, proper positioning of the patient in relation to the care provider, and awareness of both the target's depth and angle from the point of probe insertion. Risks of unsuccessful placement of a probe can range from minor complications, such as patient anxiety and discomfort due to repetition of the procedure following incorrect initial placement, to severe complications, such as pneumothorax, arterial or venous laceration, or delay of delivery of life-saving fluids or medications in an emergency situation.

Ultrasound guided techniques and devices have been developed to aid in correct placement of percutaneous probes. Ultrasound guided techniques usually require two people, an ultrasound operator who locates the internal target and keeps an image of the target centrally located on a monitor, and a care provider who attempts to guide the probe to the target based upon the sonogram. Such techniques are very difficult perceptually. For instance, these techniques are complicated by the fact that the person targeting the tissue with the probe is not the same person as is operating the ultrasound. In addition, the generally thin, cylindrical probe is usually small and reflects very little of the ultrasound beam. Moreover, as the cylindrical probe and the ultrasound beam are not generally normal to one another, the small amount of ultrasonic energy that is reflected from the probe will reflect at an angle to the incident beam, resulting in little if any of the reflected energy being detected by the ultrasound transducer. As a result, the probe itself is difficult to visualize in the sonogram and the person placing the probe must attempt to guide the probe to the correct location using minimal visual feedback provided by the ultrasound operator physically rocking the ultrasound transducer. Rocking the transducer allows the observer to see a series of planar sonograms of the internal region, and, with training, the observer can learn to recognize subtle changes in the sonograms as the probe deflects and penetrates the surrounding tissue and pick up subtle ultrasonic shadow artifacts deep to the probe created when the probe blocks the transmission of the ultrasound beam to the tissue below.

In an attempt to relieve the difficulties of ultrasound guided probe techniques, systems have been developed including a probe guide which can be attached to an ultrasound transducer housing. Problems still exist with such devices however. For instance, the probe guide is to one side of the ultrasound transducer housing in these devices, and the probe is often inserted at a fixed angle to the plane of the ultrasound beam displayed on the sonogram, restricting the intersection of the ultrasonographic beam and the point of the probe to a very small area in space. In addition, and as with hand-guided ultrasound techniques, very little, if any, ultrasonic energy is reflected from the probe back to the transducer. In fact, due to the angle between the incident ultrasonic beam and the probe in these devices, visual cues to the location of the probe tip may be even more difficult to discern on a sonogram when using these devices. In addition, in many of these devices, the probe passes through the ultrasound beam at a fixed depth range depending on the set angle of the probe guide, and this may not correspond to the depth of the target, in which case it may not be possible to show the juncture of the target and the probe tip on the sonogram at all.

What is needed in the art is an improved device and method for utilizing ultrasound to guide a probe to a percutaneous target.

Another problem that exists when attempting to place a percutaneous probe concerns movement of the probe following correct placement. For instance, after successfully placing a probe, in many procedures it is desirable for the probe tip to remain at the target location for a period of time, for instance as a catheter wire is inserted or a biopsy taken. Often, a small movement of the hand holding the probe in place can cause the probe tip to shift away from the target, leading to complications. Thus, what is needed in the art is a device and method that can clamp a probe following placement in order to limit motion of the probe tip within the body.

Yet another on-going problem faced by medical professionals everywhere is maintenance of a sterile field during procedures. Thus, what is additionally needed in the art is the ability to maintain a sterile field while utilizing ultrasound guided probe devices and methods.

SUMMARY OF THE INVENTION

For purposes of this disclosure, the term "probe" is herein defined to be device that can be guided by and used in conjunction with the ultrasound devices of the present invention. For example, the term "probe" can refer to a needle, a tube, a biopsy device, or any other item that can be guided by the devices as herein described.

In addition, the term "probe device" is herein defined to be a device that can be utilized with a probe, but does not necessarily include the probe itself.

In one embodiment, the present invention is directed to a probe device that can include an ultrasound transducer housing which can include an ultrasound transducer for transmitting an ultrasonic beam. The ultrasound transducer housing can define a probe guide opening through the base of the housing. The probe guide opening can pass through the area defined by the ultrasound transducer or outside of this area, depending upon the desired characteristics of the system.

The device can, in one embodiment, also include a sterile seal that can be removably attached to the ultrasound transducer housing. The sterile seal can include, for example, a sterile probe guide that can be removably received within the probe guide opening.

The sterile seal can also include a seal base, onto which the base of the ultrasound transducer housing can fit. In one embodiment, the sterile seal can include a sterile sleeve, which can be adapted for substantially covering the exterior of the ultrasound transducer housing without blocking movement of a probe through the probe guide. For example, the sterile sleeve can include a pliant, disposable material such as a nonwoven web material or a thermoplastic material.

In one embodiment, the medical probe device can be a linear, noninvasive probe device incorporating a linear ultrasound array such as is generally known in the art for visualizing vascular targets. In one particular embodiment, the probe guide opening defined by the transducer housing can be perpendicular to the flat base of the linear array device. In another embodiment, the medical probe device can be a convex device, in which the array of elements forming the ultrasound transducer defines an arcuate profile. In some embodiments, the base of the device can also define an arcuate profile that can correspond to the curvature of the ultrasound transducer within the transducer housing. Such devices are often common for visualizing large targets, such as organ visualization devices. In one particular embodiment of a convex probe device, the probe guide opening can be perpendicular to the tangent of the base taken at the point where the probe guide opening passes out of the housing at the base.

The medical probe device of the present invention can include a clamp. In one particular embodiment, the clamp can be a mechanical clamp in communication with the ultrasound transducer housing for clamping a probe in the probe guide.

In another embodiment, the medical probe device can include a detector, such as a motion detector, in communication with a processing unit. For example, the detector can detect motion of a probe as it is guided through the probe guide and communicate that information via a data stream to the processing unit. The processing unit can also be in contact with the ultrasound transducer and can be utilized to form the sonogram. The processing unit can use the information in the data stream to display information on a monitor relating the location of the probe in relation to the target. For example, the data stream can be utilized to form a real time virtual image of the probe as it moves through the field and display an image of the probe on the sonogram. In general, in this embodiment, the path of the probe can define a line that is parallel to the plane displayed on the sonogram.

In one embodiment, rather than or in addition to information concerning the real time location of the probe, information concerning the probe path can be displayed on the monitor. For example, a targeting line showing the path the probe will take, which is parallel to the plane of the sonogram, can be displayed on the monitor.

In another embodiment, the present invention is directed to a sterile seal that may be utilized in conjunction with an ultrasound device. For example, the sterile seal can include a sterile probe guide for use with an ultrasound device in order to provide a sterile barrier between the ultrasound transducer housing and a probe guided through the housing. The sterile probe guide can, in one embodiment, include separable top and bottom portions which can be attached together when the seal is received within the probe guide opening that is defined by the ultrasound transducer housing. In one embodiment, the sterile seal can include a sterile sleeve continuous from the sterile probe guide that can substantially enclose the ultrasound transducer housing without blocking motion of a probe through the sterile probe guide. For example, the sterile sleeve can comprise a pliant material that can wrap the ultrasound transducer housing and/or the sleeve can comprise a non-pliable base that can cover one or more surfaces of the transducer housing. In one embodiment, a clamp for clamping a probe in the sterile probe guide can be integral to the sterile seal.

The presently disclosed devices may be utilized in a variety of medical procedures. For example, the devices may be utilized to target blood vessels, tissue masses, or fluid-filled cavities. In one particular embodiment of the present invention, the devices may be utilized during central venous catheterization procedures.

BRIEF DESCRIPTION OF THE FIGURES

A full and enabling disclosure of the present invention, including the best mode thereof to one of ordinary skill in the art, is set forth more particularly in the remainder of the specification, including reference to the accompanying figures in which.

Figure 1:
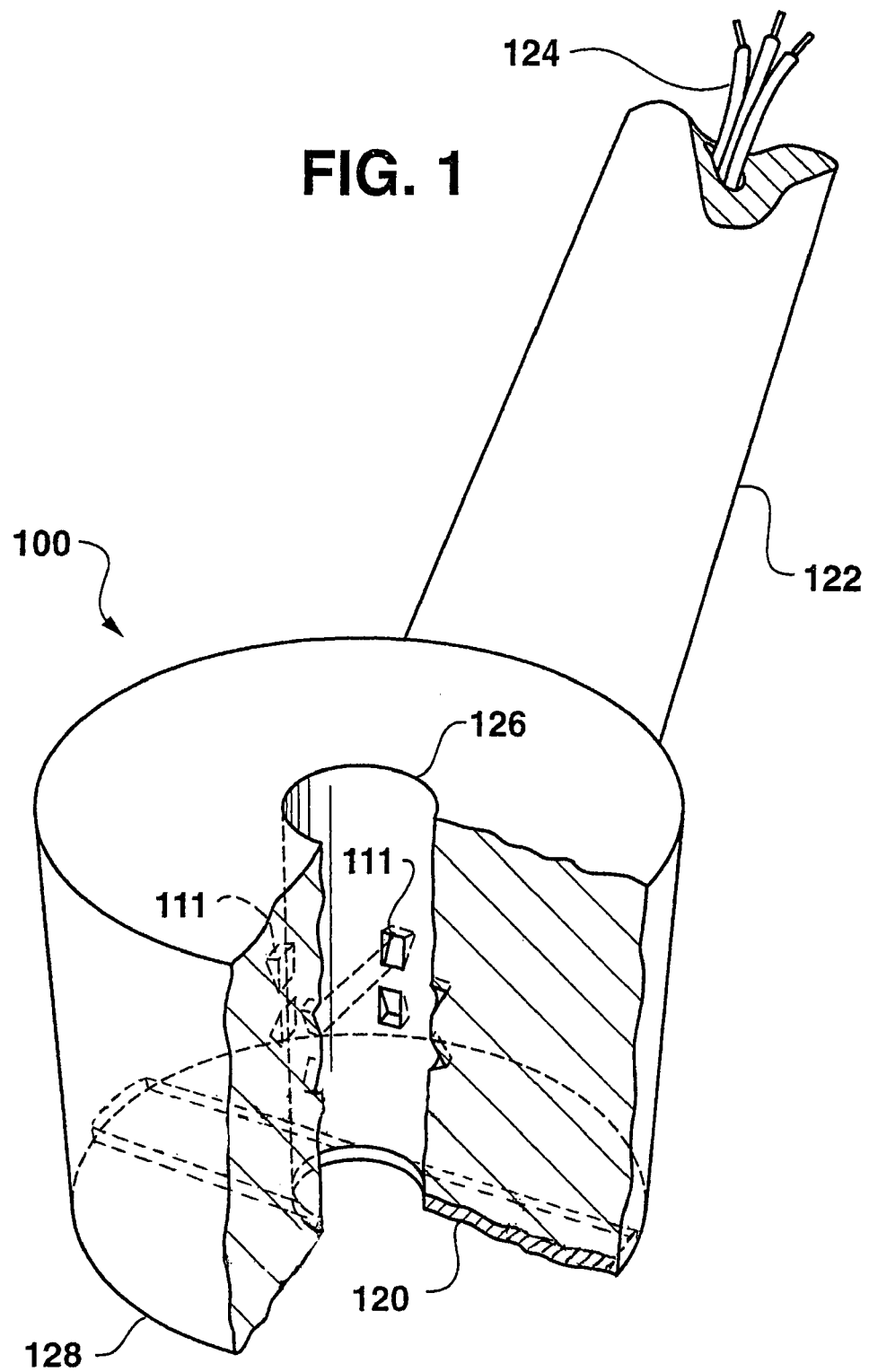
FIG. 1 illustrates one embodiment of an ultrasound transducer housing of the present invention.

Repeat use of reference characters in the present specification and drawings is intended to represent the same or analogous features of elements of the invention. Other objects, features and aspects of the present invention are disclosed in or are obvious from the following detailed description.

DETAILED DESCRIPTION OF PREFERRED EMBODIMENTS

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment. Thus, it is intended that the present invention cover such modifications and variations as come within the scope of the appended claims and their equivalents.

The present invention is directed to improved devices and methods for use in guiding percutaneous probes during medical procedures. More specifically, the ultrasound devices of the present invention include an ultrasound transducer housing having an opening therethrough configured to accommodate a probe. In one embodiment, the opening can serve as a probe guide. Optionally, the opening can be configured to accommodate a removable probe guide for the probe.

Using the presently disclosed devices, the path of a probe guided through the device and hence the location of the probe tip can be more clearly known in relation to a target imaged by the ultrasound device. In addition, in one preferred embodiment, the presently disclosed devices can be utilized by a single operator who can control both the ultrasound transducer and the probe during the procedure.

Using the presently disclosed devices, a probe tip can be guided to a percutaneous target on a line that is parallel to the plane imaged on the sonogram. That is, either within the plane imaged on the sonogram or adjacent to it, but in either case parallel to it. When utilizing the presently disclosed devices, the path of the probe to the target can be known, even if it cannot be discerned on the sonogram: the probe will advance toward the target on a straight line and at a predetermined angular relationship to the ultrasound housing base from the probe guide opening that is defined by the transducer housing, past the exit of the probe guide opening, and, while traveling parallel to a plane that can be imaged on a sonogram, to the target that is imaged by the ultrasound. Thus, the path of the probe and the sonogram image can both be defined by the orientation of the transducer and can be coordinated on the target. In order to strike the target, the probe can be merely guided along this known path the desired distance. In one particular embodiment of the invention, the path of the probe can be perpendicular to the base of the ultrasound transducer housing at the probe guide opening exit. By use of the disclosed targeting devices, the guesswork and difficulties of previously known ultrasound guided procedures due to the angle between the advancing probe and the image formed by the ultrasonic beam can be removed.

In one embodiment of the present invention, the targeting process can be even further improved by the creation of an image of the known path of travel of the probe or an image of the advancing probe itself, a 'virtual probe', either of which can overlay the sonogram formed by the ultrasound device. In one particular embodiment, a motion detector can register motion of a probe in the probe guide, and that information can be displayed, for instance, as a real time image of the probe on a screen or monitor. In this embodiment, the location of the probe tip in relation to the target and the moment when the probe tip strikes the target can be seen in real time by an operator watching the virtual probe on the monitor during the procedure.

In one embodiment, the presently disclosed invention is directed to a sterile seal which can cover surfaces of an ultrasound transducer housing that may be near the patient and/or the probe. Beneficially, the sterile seal of the present invention can include a sterile probe guide. During the procedure, the sterile probe guide can be located within the probe guide opening that passes through the ultrasound transducer housing. During a probe insertion procedure, the probe can pass through the sterile probe guide and not come into contact with the ultrasound transducer housing. The presence of a sterile barrier between the ultrasound transducer housing and the probe during the procedure can greatly enhance patient safety by prevention of infection. In addition, in one embodiment, the sterile seal can include a sleeve to substantially cover the ultrasound transducer housing. Thus, due to the presence of the sterile seal, the ultrasound transducer housing and related equipment need not be sterilized after a procedure, and can be ready to be used again with a new sterile seal after a simple cleansing procedure. As such, a single ultrasound transducer may be used more frequently, making the devices much more economical.

A removable probe guide is not a requirement of the present devices, however. In other embodiments, the probe guide may be the probe guide opening. In any case, the presently disclosed devices can be utilized to guide a probe on a known path of travel from the housing itself directly toward a target.

It should be understood as well that the sterile seal of the present invention, while particularly well suited for use with the ultrasound devices as herein disclosed, can also be utilized with other ultrasound transducers in which a probe guide opening is defined by the ultrasound transducer housing.

Following successful insertion of a percutaneous probe to a target, many procedures require the probe to remain at the target for a period of time. For example, during the Seldinger technique common for central venous catheter placement, a cannulated needle attached to a syringe is first guided into a vein. After the needle tip is in the lumen of the vein, the needle is held while the syringe is removed from the needle and a guide wire is fed down through the needle and into the vein. During this process, only a slight movement of the needle can cause the needle tip to move out of the vein, and the entire procedure must be repeated.

In order to prevent such motion of the probe tip following insertion to a target, one embodiment of the present device includes a clamp for the probe. In this embodiment, the device can include a clamp which can firmly hold the probe in relation to the ultrasound transducer housing and prevent motion of the probe during subsequent procedures such as catheter insertion, biopsy procedures, fluid or gas aspiration, or the like. As the ultrasound transducer housing can be much easier to hold in place during such procedures as compared to holding only the small probe, motion of the probe tip can be much less likely when the probe is securely clamped in relation to the ultrasound transducer housing and the transducer housing is held in the hand and further stabilized by patient contact as compared to when only the probe by itself is held in the hand In accord with the present invention, FIG. 1 illustrates one embodiment of an ultrasound transducer housing generally 100 according to the present invention. In this embodiment, the transducer housing includes an ultrasound transducer generally 120 that transmits and receives ultrasonic waves. The ultrasound transducer 120 can be any type of ultrasound transducer as is generally known in the art. For example, in one embodiment, the ultrasound transducer can be a piezoelectric transducer formed of one or more piezoelectric crystalline materials arranged in a two or three-dimensional array. Such materials include ferroelectric piezoceramic crystalline materials such as lead zirconate titanate (PZT). In one embodiment, the elements that form the array can be individual electrode or electrode segments mounted on a single piezoelectric substrate, such as those described in U.S. Pat. No. 5,291,090 to Dias, which is incorporated herein by reference thereto. In general, the ultrasound transducer 120 can be formed of multiple elements, however, single crystal devices are also encompassed by the present invention.

The use of multiple element ultrasound transducers can be advantageous in certain embodiments, as the utilization of multiple elements can provide an ultrasound transducer in which the individual elements that make up the array can be controlled so as to limit or prevent any break or edge effects in the sonogram which could otherwise occur in those embodiments wherein the probe guide opening passes through the transducer, e.g., a break in the array of elements forming the transducer. For instance, in the present devices, the firing sequence of the individual crystals can be manipulated through various control systems and prevent any possible 'blind spots' in the sonogram as well as to clarify the edges of individual biological structures in the sonogram. Such control systems are generally known in the art and thus will not be described in detail.

Ultrasound transducer housing 100 defines a probe guide opening 126 that is substantially perpendicular to both the base 128 of the ultrasound transducer housing 100 as well as to the plane of the linear ultrasound transducer 120. As such, in this particular embodiment, a probe that is guided through the probe guide opening 126 can travel parallel to the plane of a sonogram formed by the device and coincident with the direction of the emitted ultrasonic beam. Thus, in this illustrated embodiment, when the ultrasound transducer housing is centered over the target, the probe can merely be guided straight down through the field to the depth of the target, and the operator can be assured of striking the target with the probe, as there is no angle of approach between the probe and the target in relation to the direction of the emitted ultrasonic beam.

Generally, the ultrasound transducer 120 can be connected via signal wires with a cable 124 that leads to a processing unit which processes the data to form a sonogram on a monitor, as is generally known in the art. In the particular embodiment as illustrated in FIG. 1, cable 124 is internal to handle 122 of the ultrasound transducer housing 100, though this is not a requirement of the invention. Handle 122 can generally be set at an angle to the base 128 of transducer housing 100 so as to be comfortably held in the hand while the device is being utilized.

As can be seen, in this particular embodiment, ultrasound transducer 120 is a linear array that is discontinuous across the base 128 of ultrasound transducer housing 100 at probe guide opening 126. A probe can be guided through probe guide opening 126 and past ultrasound transducer 120 in a path that is substantially perpendicular to ultrasound transducer 120.

Figure 10A:
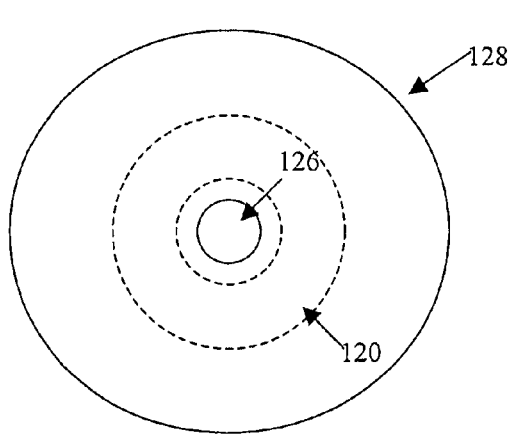
FIGS. 10A-10F are planar views of embodiments of ultrasound transducers of the present invention, showing a variety of relationships between the ultrasound transducer and a probe guide opening defined by the transducer housing.
Figure 10B:
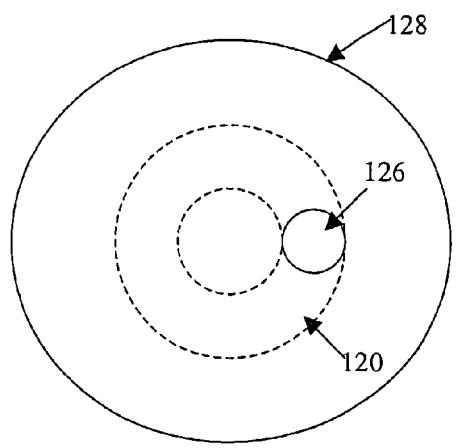
Figure 10C:
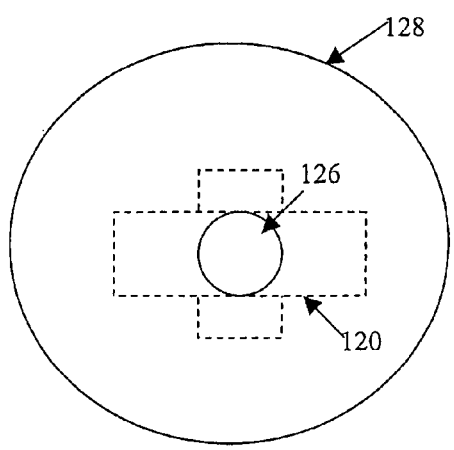
Figure 10D:
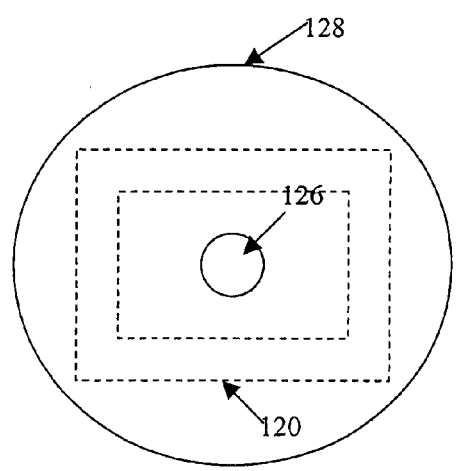
Figures 10E, 10F:
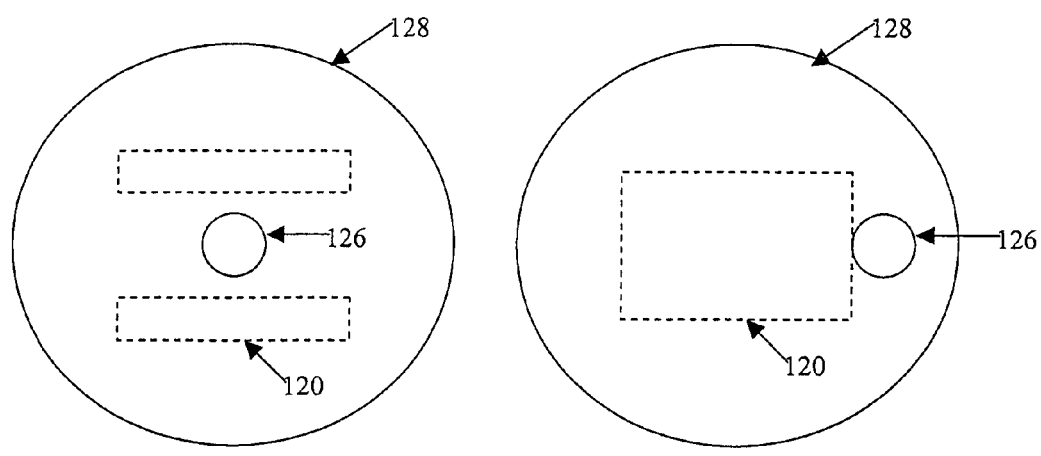
Figure 11:
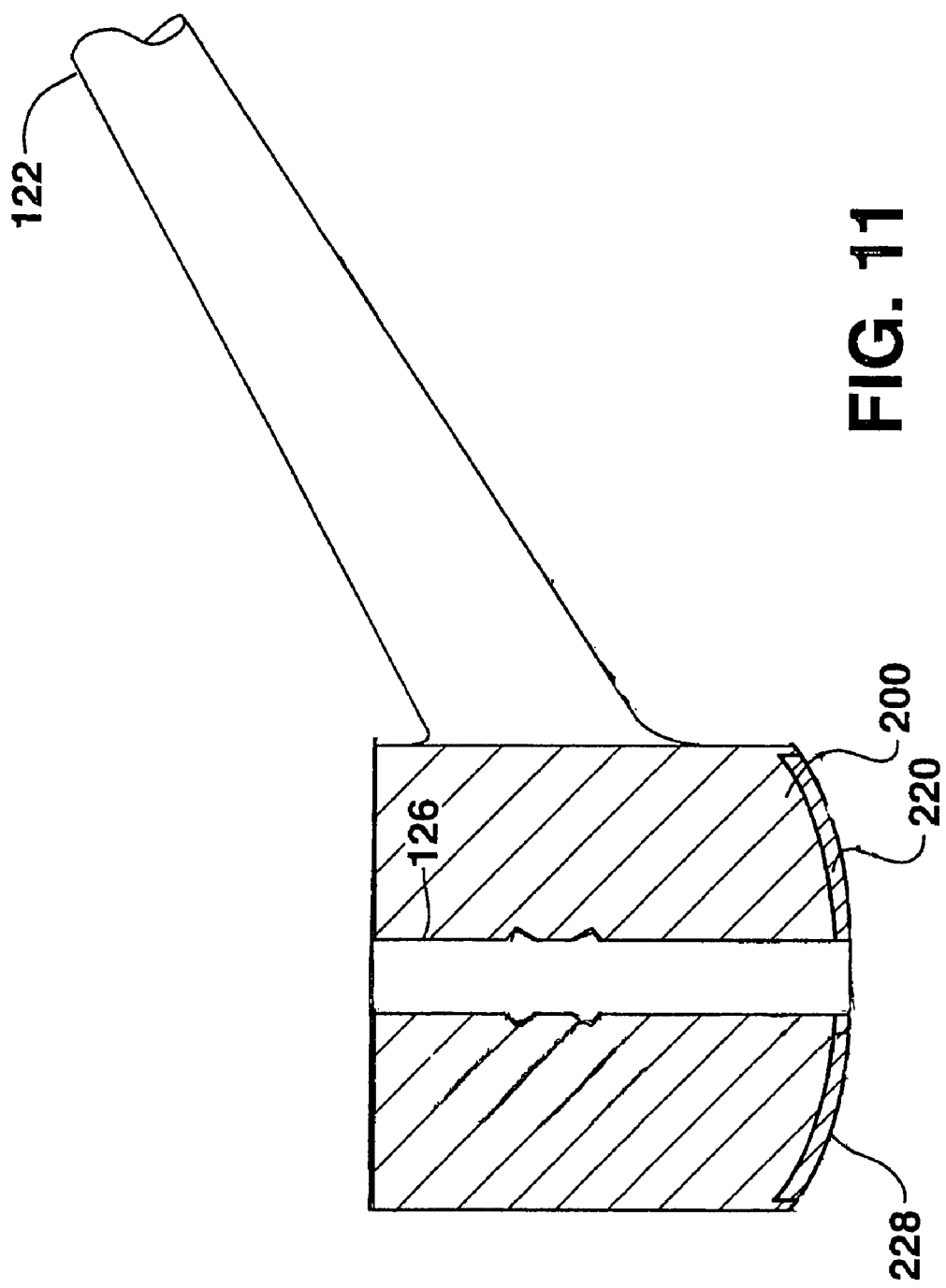
FIG. 11 illustrates another embodiment of the ultrasound transducer housing of the present invention including a convex ultrasound transducer.

In other embodiments, the geometric arrangement of the ultrasound transducer may be varied, as can the location of the probe guide opening in relation to the transducer, as long as the probe guide opening is defined by the ultrasound transducer housing and passes through the base of the transducer housing. For example, while not meant to be in any way limiting, FIGS. 10A-10F illustrate plan views of several exemplary orientations for ultrasound transducers 120 of the disclosed devices as well as relative locations for probe guide openings 126 through the base 128 of the transducer housing. FIG. 10A includes a generally circular ultrasound transducer 120. In this embodiment, the probe guide opening 126 can pass through the area enclosed by the transducer, but at the center, such that there is no break in the transducer itself. Alternatively, as shown at FIG. 10B the probe guide opening 126 can pass through the ultrasound transducer 120 at a break in the transducer. FIG. 10C illustrates another possible geometric arrangement for the transducer. In this embodiment, the ultrasound transducer 120 is generally of a T-shape, with the probe guide opening 126 at the center of the intersection of the two linear portions of the ultrasound transducer 120. In yet another alternative embodiment, shown in FIG. 10D, the ultrasound transducer 120 is rectangular, with the probe guide opening 126 at the center of the rectangular array. FIG. 10E illustrates another embodiment in which the ultrasound transducer 120 is comprised of two separated sections, with the probe guide opening 126 between the two sections of the array. In yet another embodiment, the probe guide opening 126 can be outside the area defined by the ultrasound transducer 120, though the path of a probe through the probe guide opening can still be parallel to the plane of the sonogram formed by the transducer in this embodiment. Any suitable planar geometric arrangement for the ultrasound transducer is encompassed by the disclosed devices, as is the location of the probe guide opening in relation to the ultrasound transducer In addition, the presently disclosed devices are not limited to linear transducers, such as illustrated in FIG. 1. In another embodiment, as illustrated in FIG. 11, the ultrasound transducer can be a convex transducer, such as is commonly used in procedures in which larger targets are imaged by the devices. Convex transducers are common, for example, in prenatal ultrasound devices and large organ scanning devices. Such devices include an ultrasound transducer having an arcuate profile, such that the ultrasound beam emitted by the device fans out in a wider field. FIG. 11 illustrates one embodiment of a convex ultrasound device according to the present invention. As can be seen, ultrasound transducer housing 200 has a convex base 228. Within ultrasound transducer housing 200 is ultrasound transducer 220, which has an arcuate profile, as shown. Ultrasound transducer housing 200 defines a probe guide opening 126 that passes through the transducer housing 200, through the arcuate base 228, and, in this particular embodiment, through the arcuate ultrasound transducer 220. In this particular embodiment, probe guide opening 126 is perpendicular to the tangent of the arcuate base 228 at the exit of probe guide opening 126. In other embodiments, the probe guide opening may alternatively be at a different angle to the tangent of the base at the opening and may be in a different orientation to the probe guide opening, as described above in relation to linear transducers.

Referring again to FIG. 1, transducer housing 100 defines probe guide opening 126 that passes through ultrasound transducer 120. Probe guide opening 126 can include recessed portions 111 where the dimensions of probe guide opening 126 are slightly increased along a short portion of the length of the probe guide opening 126. Recessed portions 111 can be used to hold a removable probe guide in the probe guide opening, as will be further disclosed herein.

It should be understood that any particular geometric configuration for transducer housing 100 and its individual sections is not essential to the present invention. For instance, though FIG. 1 illustrates both ultrasound transducer housing 100 and probe guide opening 126 both with a substantially cylindrical shape, any other shape could be equally utilized. For example, the base 128 of transducer housing 100 may be oblong, square, or any other suitable shape. In addition, ultrasound housing 100 may extend substantially vertically when placed on a surface, as shown in the figures, or may be canted at an angle when the base 128 is placed flat on a surface. In certain embodiments, the shape of ultrasound housing 100 may be particularly designed to fit specific locations of the anatomy. For example, ultrasound housing 100 may be shaped to be utilized specifically for infraclavicular approach to the subclavian vein, approach to the internal jugular vein, or some other specific use.

In addition, though in preferred embodiments probe guide opening 126 can be perpendicular to the flat linear base 128 of a linear transducer housing as shown in FIG. 1 this is not a requirement of the invention. In other embodiments, the probe guide opening defined by the ultrasound transducer housing and passing through the ultrasound transducer housing base can be at some other angle to the base at the probe guide opening.

Figure 2:
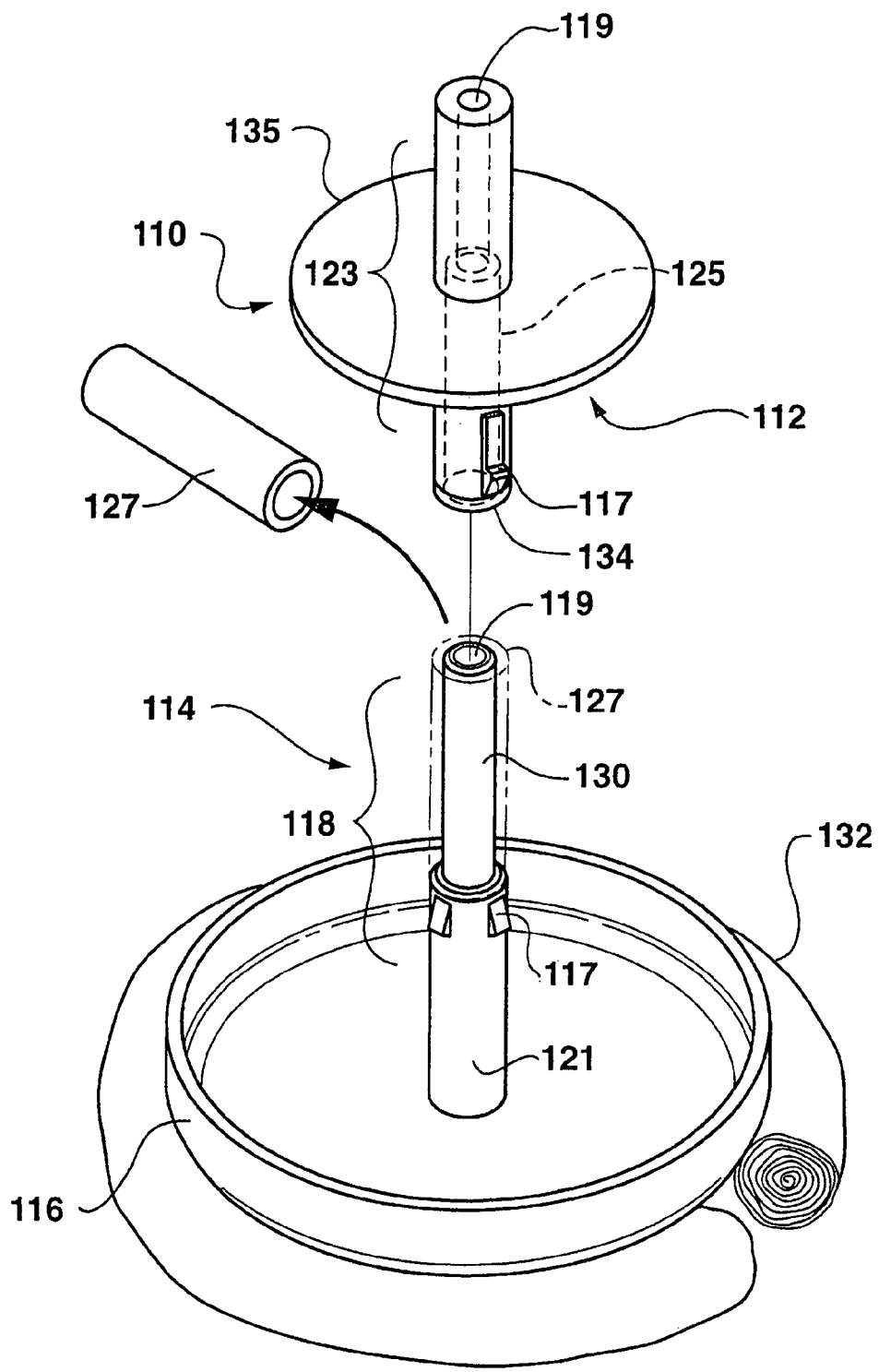
FIG. 2 illustrates one embodiment of a sterile seal according to the present invention including separable top and bottom portions.

In one embodiment, probe guide opening 126 can serve as a probe guide for a probe directed to a target. In another embodiment, a removable probe guide can be placed in the probe guide opening. For example, one embodiment of the present invention includes a sterile seal including a sterile probe guide that can be removably attached within the probe guide opening of a transducer housing. FIG. 2 illustrates one particular embodiment of a sterile seal, generally, 110 that can be utilized in cooperation with ultrasound transducer housing 100 to provide a sterile barrier between a patient and the ultrasound transducer housing 100 during a medical procedure. Sterile seal 110 includes separable top piece, generally, 112 and bottom piece, generally, 114. Sterile seal 110 can be formed of a number of different materials which can be sterilized. For instance, sterile seal 110 can be formed of sterile, single-use materials as are generally known in the art such that the entire sterile seal 110 can be properly disposed of following a single use.

Sterile seal 110 includes bottom piece 114 that includes a seal base 116 formed of an ultrasonic transmissive material. Seal base 116 can be of any suitable size and shape. In general, seal base 116 can be between about 0.5 inches and about 6 inches on its greatest length. For example, the seal base 116 can be about 0.5 inches on its greatest length so as to promote stability of the device during use. In other embodiments, it can be larger, however, such as about 1 inch on its greatest length, about 2 inches on its greatest length, or even larger. In addition, seal base 116 can generally be of the same geometric shape as the base 128 of ultrasound transducer housing 100 in order that ultrasound transducer housing base 128 may be seated firmly in seal base 116 and not slide about during use.

Arising out of seal base 116 is lower portion 118. Lower portion 118 defines a portion of probe guide 119 therethrough. Probe guide 119 extends completely through both lower portion 118 and seal base 116. Lower portion 118 includes a lower section 121 having a cylindrical exterior and an upper section 130 having a smaller cylindrical exterior. Section 130 may include a removable cap 127 for protection of the sterile surface of probe guide 119 during assembly of sterile seal 110 with ultrasound transducer housing 100. Lower portion 118 also includes tabs 117 that can be utilized when assembling sterile seal 110 with ultrasound transducer housing 100, as will be further described herein.

The bottom piece 114 of sterile seal 110 also includes sterile drape 132. Sterile drape 132 can be glued or otherwise attached to seal base 116. Sterile drape 132 can generally be formed from any of a number of suitable flexible, pliant materials such as woven or nonwoven web materials commonly used for sterile drapes or sheeting, or may be formed of any other suitable sterilizable, pliant natural or synthetic material. Sterile drape 132 is shown in a rolled configuration in FIG. 2. Sterile drape 132 can be unrolled to cover the upper surfaces of the transducer housing 100 during assembly of sterile seal 110 with transducer housing 100 and provide a portion of the sterile barrier between the transducer housing 100 and a patient during a procedure. In this embodiment, sterile drape 132 and sterile base 116 together form a sterile sleeve continuous from one end of the sterile probe guide 119 that can substantially cover the outer surfaces of an ultrasound transducer housing 100.

Sterile seal 110 also includes top piece 112. Top piece 112 includes upper portion 123 defining an upper section of probe guide 119 at one end of upper portion 123 and a slightly larger passage 125 continuous with and below the upper section of probe guide 119. The larger passage 125 is sized so as to snugly reside over upper section 130 of lower portion 118 with the base 134 of upper portion 123 sitting on the top of section 121 when top piece 112 and bottom piece 114 are combined during assembly of sterile seal 110. In order to assemble sterile seal 110, cap 127 can be removed from section 130 of lower portion 118, and upper portion 123 may slide over lower portion 118 to form uninterrupted probe guide 119 extending from the top of top piece 112 all the way through the seal base 116 of the bottom piece 114. Top piece 112 also includes shield 135 and tabs 117, the use of which can be further understood with reference to FIG. 3.

Figure 3:
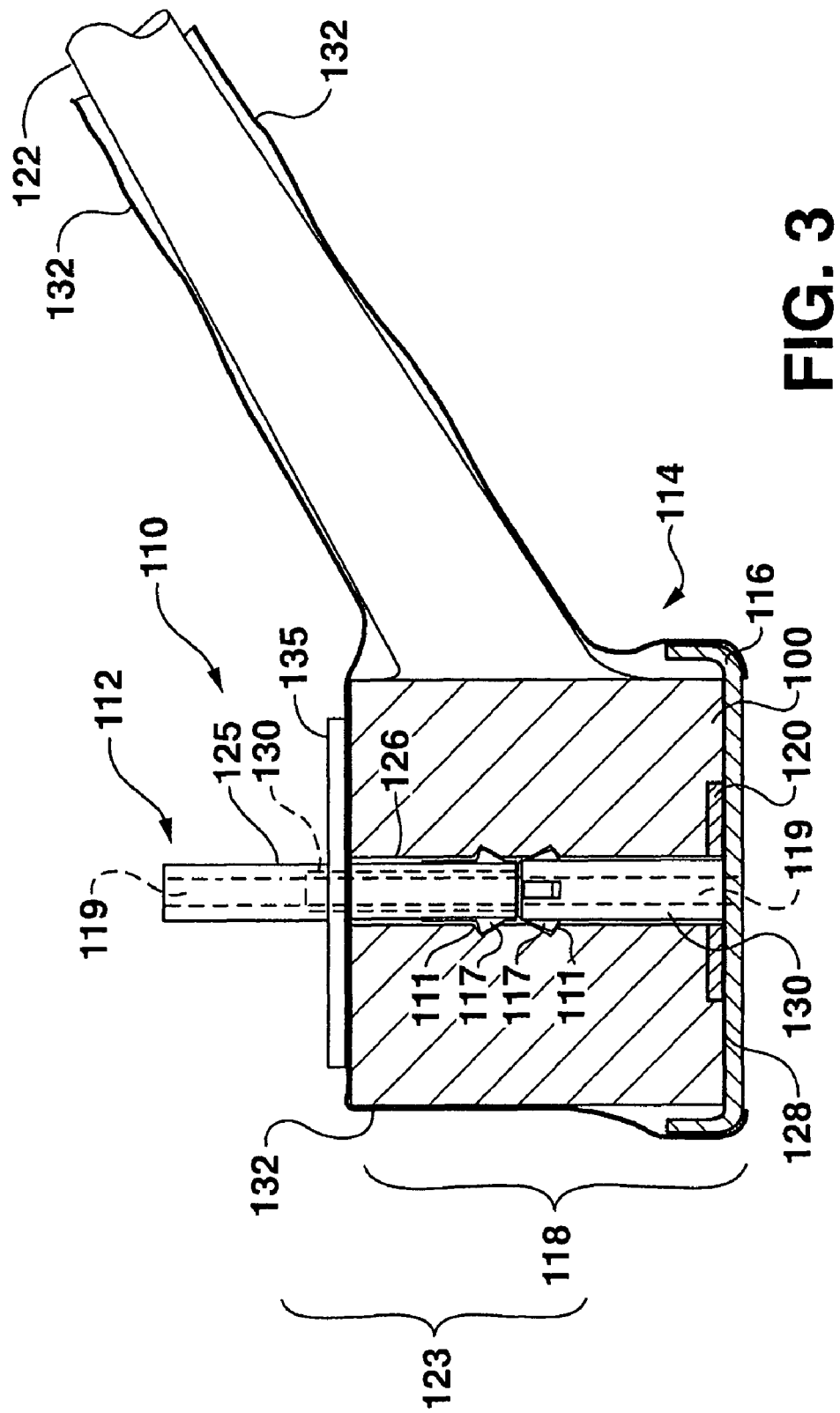
FIG. 3 illustrates one embodiment of a device of the present invention including an ultrasound transducer housing enclosed by a sterile seal so as to form a sterile probe guide within the probe guide opening that is defined by the ultrasound transducer housing.

FIG. 3 illustrates a cut-away view of one embodiment of the present invention including ultrasound transducer housing 100 held within fully assembled sterile seal 110 including top piece, generally, 112 and bottom piece, generally, 114 of sterile seal removably attached to each other. In order to better understand the combined configuration illustrated in FIG. 3, the assembly process for this particular embodiment will now be described in detail.

Ultrasound transducer housing 100 defining probe guide opening 126 is seated in seal base 116 of sterile seal bottom piece 114 such that lower portion 118 extends through transducer housing probe guide opening 126. Generally, section 130 of lower portion 118 will be covered with a protective cap 127 (as seen in FIG. 2) during this portion of the assembly process. Lower portion 118 should generally be of a length such that after ultrasound transducer housing 100 has been seated on seal base 116, lower portion 118 can pass completely through probe guide opening 126 with a portion of section 130 extending beyond the top of ultrasound transducer housing 100. Generally, a small amount of an ultrasonic gel can be placed between transducer housing base 128 and seal base 116 during seating to prevent any air between the two and promote transmission of the ultrasonic waves. As transducer housing 100 is slid over lower portion 118, tabs 117 can slide or snap into recesses 111, helping to lock together the sterile seal bottom piece 114 and transducer housing 100. After ultrasound transducer housing 100 is located on bottom piece 114 of sterile seal 110, sterile drape 132 can be unrolled to cover the top of transducer housing 100 including at least a portion of handle 122. Sterile drape 132 can define a small opening of a size so as to allow that portion of section 130 which extends beyond the top of ultrasound transducer housing 100 to pass through the sterile drape 132 when unrolled. At this time, protective cap 127 (not shown in FIG. 3) can be removed from lower portion 118 and upper portion 123 can be slid onto lower portion 118 and into the transducer housing probe guide opening 126, such that passage 125 snugly fits over section 130. Tabs 117 can snap or slide into recesses 111 and help lock sterile seal top piece 112 into transducer housing probe guide opening 126. Shield 135 can press sterile drape 132 against the top of ultrasound transducer housing 100 helping to ensure the sterile barrier.

Following the above described assembly process, probe guide 119 can extend continuously from the top of sterile seal top piece 112 through the seal base 116. Moreover, and of great benefit to the invention, probe guide 119 can be sterile and yet still within ultrasound transducer housing 100 such that the path of a probe guided through probe guide 119 can be known in relation to the sonogram formed by use of ultrasound transducer 120.

Following the procedure, sterile seal 110 can be disassembled merely by reversal of the assembly process. Tabs 117 can be retractable by pulling, twisting, or some other lever action, allowing the upper portion 123 and lower portion 118 to be removed from the probe guide opening.

It should be understood that the sterile seal of the present invention can be designed with particular characteristics so as to conform to any shape for any ultrasound transducer housing as is known in the art. For example, in other embodiments, the upper and lower pieces of a sterile seal may be of unitary construction, and need not be removably attached to each other but may rather integral with each other. In addition, a sterile seal may consist of only a sterile probe guide as can be placed within the probe guide opening defined by a transducer housing. In other embodiments, a sterile sleeve can be formed entirely of a pliant sterile drape that is continuous from one end of the sterile probe guide 119. In other embodiments, a sterile sleeve can be formed of other materials, such as a formed thermoplastic material, for example. In such an embodiment, the sterile sleeve could, for instance, include non-pliable top and bottom portions that could be snapped or otherwise attached to each other to substantially cover an ultrasound transducer housing, while defining a passage therethrough such that movement of a probe through the probe guide opening is not impeded by the presence of the sterile sleeve. Obviously, a great number of possible configurations of the sterile seal may be equally effective, the only requirement being that the sterile seal includes a sterile probe guide that can be removably received within the probe guide opening of the transducer housing.

In one embodiment, the ultrasound transducer housing may be hinged on an axis, for instance an axis parallel with the probe guide opening. In this particular embodiment, the ultrasound transducer housing can have a clamshell like configuration that can close about a unitary sterile probe guide or even to form the probe guide itself. In another possible embodiment, the ultrasound transducer housing can have an open slot leading from an edge of the transducer housing to the transducer housing probe guide opening. In this embodiment, a separable, unitary sterile probe guide may be slid into the transducer housing probe guide opening from the side via this slot. The ultrasound devices of the present invention encompass any configuration in which the ultrasound transducer housing defines a probe guide opening which passes through the base of the transducer housing.

According to one embodiment of the present invention, the ultrasound probe device may include a clamp. A clamp may be of any suitable configuration which may, in one embodiment, be in mechanical communication with the transducer housing to firmly hold a probe in the probe guide opening and limit or prevent motion of a probe tip. This may be especially beneficial after insertion of a probe to an internal target when it is preferred to have as little motion of the probe tip as possible during subsequent procedures. For example, during central venous catheterization, after initial puncture of the vein by the cannulated needle and prior to insertion of the long guide wire into the vein, motion of the probe tip can cause the tip to move out of the vein and necessitate repetition of the entire procedure.

Figures 4, 5:
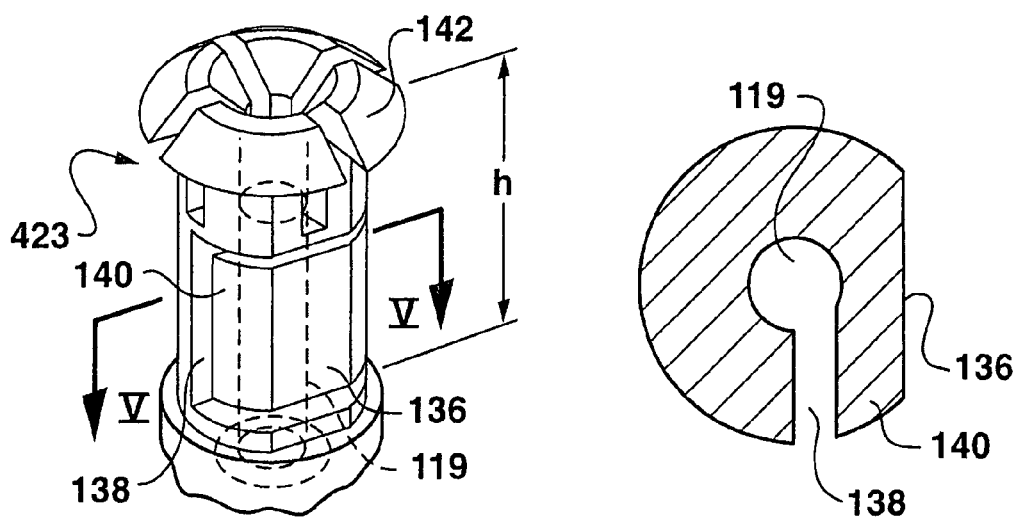
FIG. 4 illustrates an isometric view of one embodiment of the top of a sterile seal probe guide according to the present invention including an integral clamp.
FIG. 5 shows a cut-away plan view of the probe guide of FIG. 4 taken along line V-V.
Figure 6:
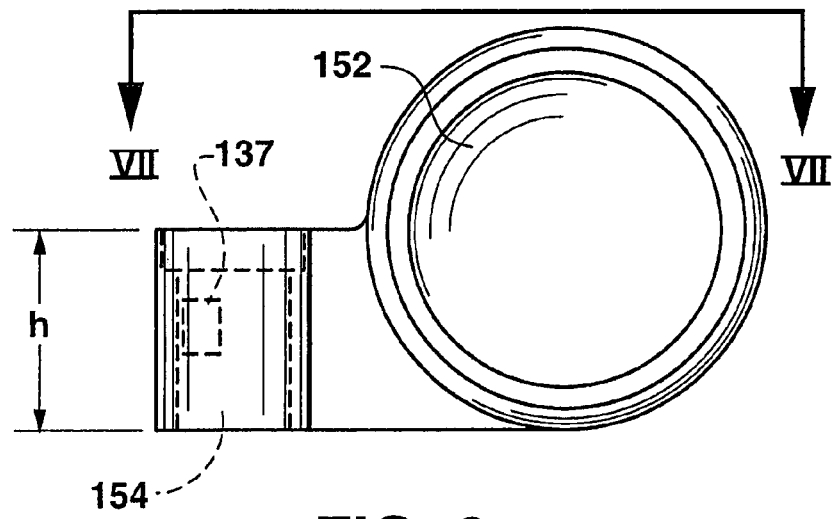
FIG. 6 illustrates a clamping lever suitable for use with the probe guide of FIG. 4.

FIGS. 4-6 illustrate one embodiment of a clamp of the present invention. Referring to the Figures, an isometric view (FIG. 4) and a cut away plan view (FIG. 5) of the terminal end of an upper portion 423 is shown. Upper portion, generally, 423 has been designed to be fitted with a clamping lever 150 shown in FIGS. 6 and 7. In this particular embodiment, upper portion 423 can be formed of a material such as a somewhat pliant plastic material that can be deformed under pressure and return to its original shape after the pressure is removed. Upper portion 423 defines a cut out 138 which extends through the wall of upper portion 423 to the depth of probe guide 119 and forms locking tab 140. Upper portion 423 also includes a cap 142 which can flex so as to allow a clamping lever 150 to be removably attached to the upper portion 423.

FIG. 5 illustrates the upper portion 423 of FIG. 4 in a cut-away plan view taken along lines V-V. As can be seen, the exterior profile of this portion of upper portion 423 is not circular. The profile of upper portion 423 includes a flat section 136. Flat section 136 extends a height 'h' (as shown in FIG. 4) along a face of upper portion 423. Cut out 138, extending from the outer surface of upper portion 423 to probe guide 119 can also be seen in the Figures. Locking tab 140 is that section of upper portion 423 immediately adjacent to cut out 138, as shown.

Figure 7:
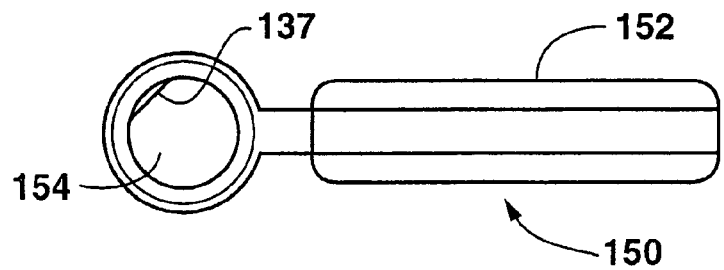
FIG. 7 shows a plan view of the clamping lever of FIG. 6 taken along line VII-VII.

FIGS. 6 and 7 illustrate a clamping lever 150 designed to slide over the cap 142 of upper portion 423. Clamping lever 150 includes a handle 152 and defines a central passage 154. Clamping lever 150 can generally be of a height 'h' so as to snuggly fit beneath the cap 142 of upper portion 423. As can be more clearly seen in FIG. 7, passage 154 includes a flat section 137 extending from the interior surface wall of passage 154 for a short distance.

Figure 8A:
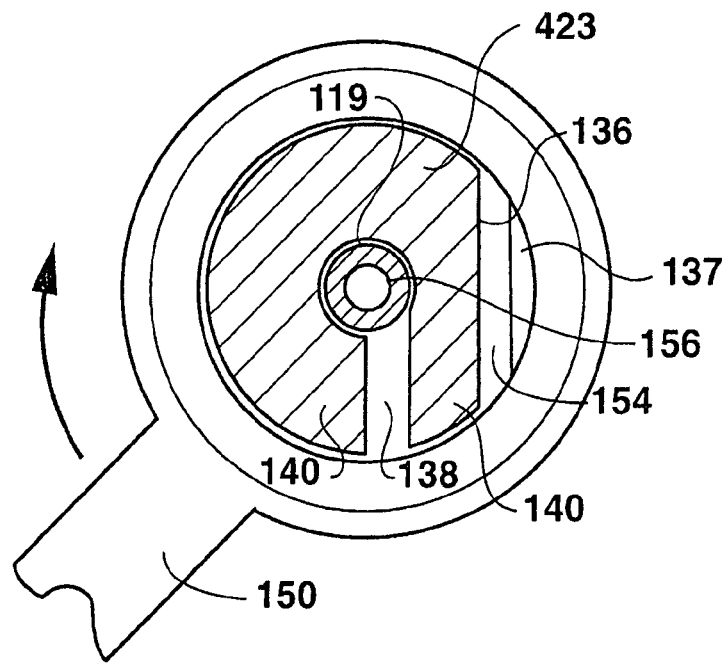
FIGS. 8A and 8B are cut-away plan views of a probe held by the clamp of FIGS. 4-7 in both an unclamped position (FIG. 8A) and a clamped position (FIG. 8B)
Figure 8B:
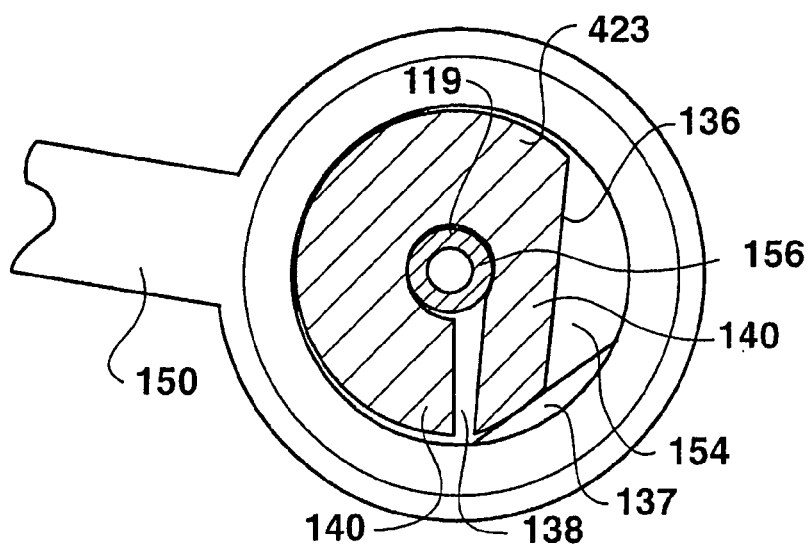

FIGS. 8A and 8B illustrate this particular embodiment of a clamp of the present invention after assembly in a plan view. Clamping lever 150 can slide over the terminal portion of upper portion 423. Cap 142 (not shown in FIGS. 8A and 8B) can hold clamping lever 150 on upper portion 423 while cannulated probe 156, can be held with a friction fit in probe guide 119 as it is slid through probe guide 119. After the probe tip has successfully reached the internal target, clamping lever 150 can be rotated, as shown by the arrow in FIG. 8A, to clamp the probe 156 within probe guide 119, as shown in FIG. 8B. As the clamping lever is rotated, flat section 137 of the clamping lever deforms locking tab 140 against the probe 156 so as to reduce the size of and/or deform probe guide 119 and tightly secure the probe 156 within probe guide 119 and limit or prevent motion of probe 156.

The figures illustrate one particular embodiment of a clamp, but it should be understood that other embodiments of a clamp are also contemplated for use with the presently disclosed probe devices, and specific geometric shapes or arrangement of components are not critical to the clamp of the present invention. For example, the clamp need not be tightened with a rotating clamping lever, as described in the embodiment above, but may optionally be activated by use of a trigger mechanism, a key, a push button, a screw, or some equivalent activation device. In one embodiment, a rotating clamping lever can include a threaded portion for tightening the clamp. For example, a rotating mechanism can be used to tighten the clamp that includes machine threads or pipe threads. Pipe threads may be preferred in one embodiment, as pipe threads can provide a secure attachment between portions of the clamp with little rotational distance required to tighten the clamp. Additionally, any suitable tensioning device could be utilized to restrict movement of the probe with respect to the transducer housing. For example, the clamp could include a set screw or a spring mechanism that can push against the probe to secure the probe in the probe guide. Additionally, the clamp can secure the probe at any point along the probe guide, near the top, as shown in the embodiment shown in the figures or optionally farther down in the transducer housing. Moreover, the clamp can be integral to a sterile seal, as shown in the figures, or used only with the ultrasound device, when no sterile seal surrounds any part of the ultrasound transducer housing. For instance, the clamp may be integral to the transducer housing or removably attachable to the ultrasound transducer housing.

In one preferred embodiment, the clamp can be manipulated by the same person as is holding the handle of the transducer housing. For instance, after insertion and placement of the probe tip at the internal target with one hand, the operator can clamp the probe in the device with the other hand, which is the same hand that is holding the transducer housing at the skin surface. Thus, in this embodiment, the entire targeting procedure may be carried out by a single individual.

Due to the basic mechanics of ultrasound devices and particularly of those of the present invention, when the probe passes through the probe guide and travels in the body and parallel to the plane imaged on the sonogram, the probe itself will be virtually invisible on the sonogram. In fact, in the embodiment wherein the probe guide is perpendicular to the base of the transducer housing at the probe guide opening, the probe can travel coincident with the direction of the beam in which case it will not be 'seen' at all by the ultrasound device. This is not a problem in the disclosed devices, however, as the entire probe path is known when looking at the sonogram. When looking at the sonogram, the base of the transducer housing will be at or near the top edge of the sonogram. Since the point of exit of the probe from the base of the transducer housing is known, and the angled relationship between the base and the probe path (i.e. the probe guide angle to the base) is known, the path the probe will take in the body is known. In order to strike the subcutaneous target with the probe, the operator need only line up this known path with the imaged target.

In one embodiment of the present invention, the known path of the probe can be added to the sonogram, and the targeting procedures can be even further simplified. For example, one embodiment of the present invention includes the addition of a targeting line on the sonogram extending from that point on the sonogram where the probe guide opening exits the housing (or passes the transducer) and projecting across the ultrasonic field in a straight line at the known angle. Thus, if this targeting line is made to intersect the target which is imaged by the device, the operator can be confident that the probe is accurately directed to the target. In other embodiments, other targeting information can be displayed on the sonogram. For example, in one embodiment, information showing the approach of the probe to the target can be displayed. For instance, in one embodiment, a real time image of a virtual probe as it travels along the known targeting line can be displayed on the sonogram.

Figure 9:
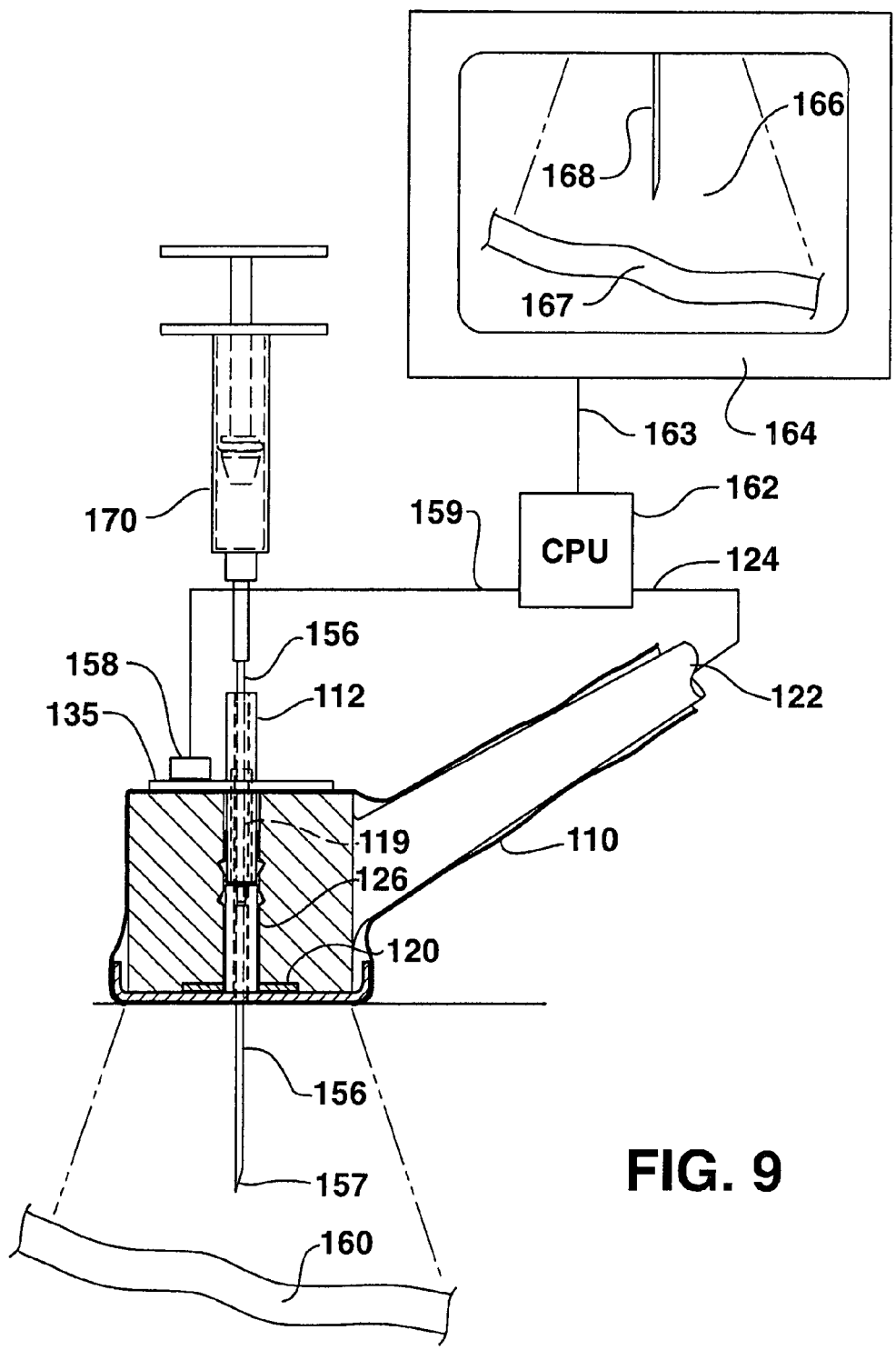
FIG. 9 illustrates another embodiment of the present invention in which an image of a virtual probe may be correlated with a sonogram.

FIG. 9 illustrates one embodiment of the present invention wherein an image of a virtual probe may be overlaid on a sonogram. In this particular embodiment, the ultrasound system can include a detector 158. Detector 158 can recognize and monitor the movement of probe 156 as it enters the ultrasound device and passes through probe guide 119 and into the body. The probe 156 can then be imaged on a monitor 164 as probe image 168. The monitor 164 can also show the sonogram 166.

A variety of different possible detectors as are generally known in the art may be utilized as detector 158. For instance, detector 158 can utilize infrared (IR), ultrasound, optical, laser, or other motion detection mechanisms. In addition, the location of detector 158 is not critical to the invention. In the embodiment illustrated in FIG. 9, detector 158 is located on shield 135 of the sterile seal 110. In other embodiments, however, the detector may be located elsewhere in the system including, for example, integral to the transducer housing 100, or elsewhere external to the transducer housing 100, such as on a portion of the probe itself.

Signals from detector 158 can be reflected off of syringe 170 or alternatively reflected off of some other portion of probe 156 to create a data stream which can be sent to processing unit 162 via information cable 159. Processing unit 162, which can be, for example, a standard lap top or desk top computer processor or part of a self-contained ultrasound system as is known in the art, can be loaded with suitable recognition and analysis software and can receive and analyze the stream of data from detector 158. The processing unit can also include standard imaging software as is generally known in the art to receive data from the ultrasound transducer via cable 124. Probe 156 can be of a predetermined length which can be input data entered into processing unit 162 by the user or can be preprogrammed into the system as a default length. Thus, through analysis of the data stream received from detector 158 and from ultrasound transducer 120, processing unit 162 can be programmed to calculate the relative position of the probe tip 157 in relation to the ultrasound transducer 120, in relation to ultrasound transducer housing base 128, in relation to detector 158 or to any other convenient reference point. Processing unit 162 can communicate this position information digitally via cable 163 to monitor 164 and the information can be displayed on the monitor such as in a numerical format or optionally as a real time image of a virtual probe 168 shown in conjunction with the sonogram 166 including an image 167 of the target, such as blood vessel 160.

In such a manner, the devices of the present invention can be utilized to actually show the approach of the probe toward the target on the monitor throughout the entire procedure. In addition, in certain embodiments, the present invention can be utilized to ensure the probe tip remains at the target during subsequent procedures. For example, in those embodiments wherein the detector 158 monitors the motion of the probe 156 via signals reflected off of probe 156, as long as probe 156 remains 'visible' to detector 158, the image 168 of probe 156 can remain on the monitor 164. Thus, in this particular embodiment, even if syringe 170 is removed to be replaced with a guide wire, as in a catheterization procedure, the image 168 of the probe 156 can remain on the monitor 164 and any motion of the probe tip 157 in relation to the target 160 can be noted by an observer.

The presently disclosed ultrasound guided probe devices and methods may be utilized in many different medical procedures. Exemplary applications for the devices can include, without limitation Central Venous Catheterization
Cardiac Catheterization (Central Arterial Access)
Dialysis Catheter Placement
Breast Biopsies
Paracentesis
Pericardiocentesis
Thoracentesis
Arthrocentesis
Lumbar Puncture
Epidural Catheter Placement
Percutaneous Intravascular Central Catheter (PICC) line placement
Thyroid Nodule Biopsies
Cholecystic Drain Placement
Arthroscopic Procedures
Laparoscopy Some of these exemplary procedures have employed the use of ultrasound in the past, and all of these procedures, as well as others not specifically listed, could utilize the disclosed ultrasound guided devices to improve procedural safety as well as patient safety and comfort, in addition to provide more economical use of ultrasound devices. In addition, the presently disclosed devices may be utilized with standard probe kits already available on the market.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A medical device for inserting a probe percutaneously comprising:
   a monitor;
   a probe configured for being guided to a subdermal location;
   an ultrasound transducer housing, said housing including an ultrasound transducer for forming a sonogram of the subdermal location on the monitor;
   a probe guide that is attachable to said ultrasound transducer housing, the probe guide defining an opening through which the probe is capable of passing, wherein upon attachment of the probe guide to the ultrasound transducer housing, the probe guide defines a barrier between the probe in the probe guide and the ultrasound transducer housing, the barrier precluding contact between the probe in the probe guide and the housing;
   at least one detector integral to the ultrasound transducer housing and configured for detecting motion of the probe in the probe guide, wherein the detector is different from the ultrasound transducer and wherein upon attachment of the probe guide to the ultrasound transducer housing the detector is at a distance from the probe guide and from the probe in the probe guide the distance being at least in part due to the barrier; and
   a processing unit in communication with the at least one detector, the monitor, and the ultrasound transducer, the processing unit configured for creating and displaying a real time image of a virtual probe, the processing unit being programmed to analyze data from the at least one detector to calculate a relative position of the probe in relation to a reference point, the processing unit being capable of communicating the relative position to the monitor, said relative position being displayed on the monitor as the real time image of the virtual probe; and
   the processing unit being further configured for displaying on the monitor the real time image of the virtual probe overlaid on the sonogram of the subdermal location.

2. The medical probe device of claim 1, further comprising an engageable clamp activatable by a user to selectively secure the probe in the probe guide.

3. The medical probe device of claim 1, wherein the at least one detector senses the presence of the probe within the probe guide.

4. The medical probe device of claim 1, further comprising a sterilizable seal removably co-operable with said transducer housing.

5. The medical probe device of claim 4, wherein the seal comprises a first piece and a second piece removably attachable to one another.

6. The medical probe device of claim 1, wherein the ultrasound transducer housing is non-invasive.

7. A method for guiding a percutaneous probe to a target comprising:
   guiding a percutaneous probe through a probe guide to a subdermal location, wherein the probe guide is attached to an ultrasound transducer housing, the probe guide forming a barrier between the probe and the ultrasound transducer housing, the barrier precluding contact between the probe in the probe guide and the housing,
   utilizing an ultrasound transducer to form a sonogram of the subdermal location on a monitor, the ultrasound transducer housing including the ultrasound transducer;
   detecting the motion of the percutaneous probe in the probe guide by use of a detector, wherein the detector is different from the ultrasound transducer and integral to the ultrasound transducer housing and the detector is at a distance from the probe guide and the probe guided through the probe guide, the distance being at least in part due to the barrier;
   creating a data stream in response to the detected motion; and
   utilizing a processing unit that is in communication with the detector, the monitor, and the ultrasound transducer to process information contained in the data stream to form a real time image of a virtual probe on the monitor, the processing unit being programmed to calculate a relative position of the probe in relation to a reference point, the processing unit being capable of communicating the relative position to the monitor, said relative position being displayed on the monitor as the real time image of the virtual probe; and
   displaying on the monitor the sonogram and the real time image of the virtual probe, the real time image of the virtual probe being displayed in conjunction with the sonogram.

8. The method according to claim 7, the method further comprising activating a clamp to grip the probe in the probe guide when the probe is at the subdermal location.

9. The method according to claim 7, the method further comprising attaching the probe guide to the ultrasound transducer housing.

10. The method according to claim 7, the method further comprising providing a sterile seal about the ultrasound transducer housing.

11. The method according to claim 7, the percutaneous probe being guided along a path, wherein the path of the probe defines a line that is within the plane of the sonogram.

12. The method according to claim 7, wherein the subdermal location is the lumen of a blood vessel.

13. The method according to claim 7, wherein the subdermal location is a tissue mass.

14. The method according to claim 7, wherein the subdermal location is a fluid-filled cavity.

15. The method according to claim 7, wherein the method is carried out by a single operator.

* * * * *

UNITED STATES PATENT AND TRADEMARK OFFICE
CERTIFICATE OF CORRECTION

PATENT NO.         : 8,152,724 B2
APPLICATION NO.    : 11/787290
DATED              : April 10, 2012
INVENTOR(S)        : Stephen F. Ridley and M. Dexter Hagy Page 1 of 1

It is certified that error appears in the above-identified patent and that said Letters Patent is hereby corrected as shown below:

In the Claims

Column 15, line 18 "housing, the probe guide defining an opening" should read --housing, the probe guide comprising one or more portions, the probe guide defining an opening--

Column 15, line 45 "image of the virtual probe overlaid on the sonogram" should read --image of the virtual probe displayed in conjunction with the sonogram--

Signed and Sealed this
Thirtieth Day of September, 2014

Michelle K. Lee
*Deputy Director of the United States Patent and Trademark Office*